Figure 4A:
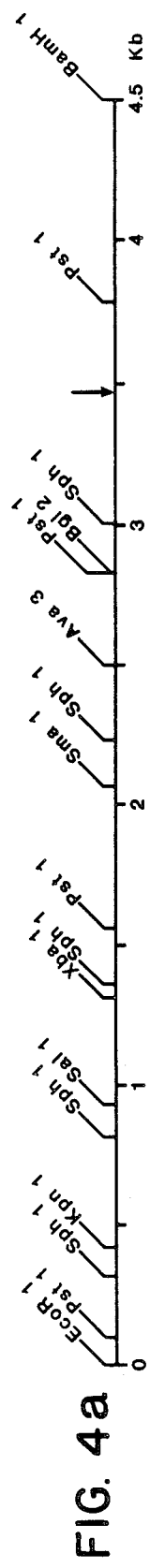

United States Patent [19]

Keith et al.

[11] Patent Number: 4,883,761

[45] Date of Patent: Nov. 28, 1989

[54] PERTUSSIS TOXIN GENE: CLONING AND EXPRESSION OF PROTECTIVE ANTIGEN

[75] Inventors: Jerry M. Keith; Camille Locht, both of Hamilton, Mont.

[73] Assignee: The United States of America as represented by the Department of Health and Human Services, Washington, D.C.

[21] Appl. No.: 843,727

[22] Filed: Mar. 25, 1986

[51] Int. Cl.[4] ............ C12N 1/00; C12N 15/00; C12N 1/20; C07H 21/04

[52] U.S. Cl. ............... 435/320; 435/172.3; 435/252.33; 536/97; 935/11

[58] Field of Search ........... 435/172.3, 70, 320; 536/27

[56] References Cited

PUBLICATIONS

Tamura et al, Biochemistry, vol. 21, pp. 5516–5522, (1982).

Unda et al, PNAS, U.S.A., vol. 81, pp. 6481–6485, Oct. 1984.

Wood et al, PNAS, U.S.A., vol. 82, pp. 1585–1588, Mar. 1985.

Semina et al, Chemical Abstracts, vol. 99:170610k, 1986 report of 1983 article.

*Primary Examiner*—Alvin E. Tanenholtz
*Attorney, Agent, or Firm*—Mishrilal Jain

[57] ABSTRACT

The complete nucleotide sequence of the pertussis toxin gene and the deduced amino acid sequences of the individual subunits have been determined. All five subunits are coded by closely linked cistrons and possibly expressed through a polycistronic mRNA, since a promotor-like structure was found in the 5' flanking region. The order of the cistrons is S1, S2, S3, S4, S5, and S3. All subunits contain signal peptides of variable length. The calculated molecular weights of the mature subunits are 25,024 for S1, 21,924 for S2, 21,873 for S3, 12,058 for S4 and 11,013 for S5. All subunits contain signal peptides of variable length. Subunits S2 and S3 share 70% amino acid homology and 75% nucleotide homology. Subunit S1 contains two regions of eight amino acids homologous to analogous regions in the A subunit of both cholera and *E. coli* heat labile toxins. Functional domains in relation to the primary structure and the development of a safer, new generation vaccine against whooping cough are presented.

3 Claims, 4 Drawing Sheets

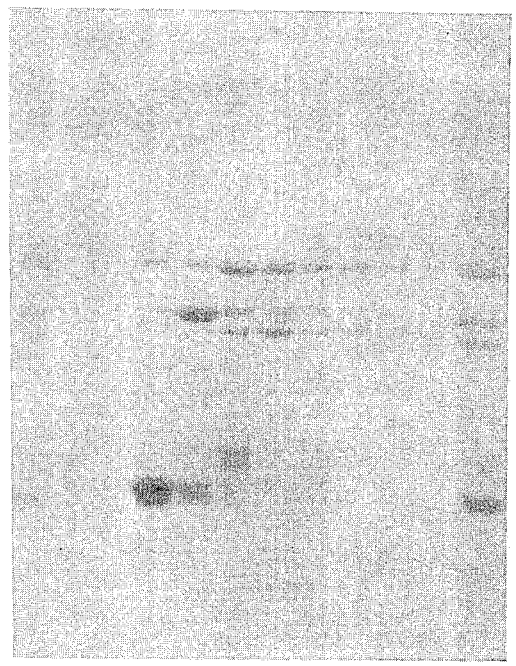
FIG. 1
-S1 28kD
-S2 23kD
-S3 22kD
-S5 9.3kD
-S4 11.7kD
FIG. 3a
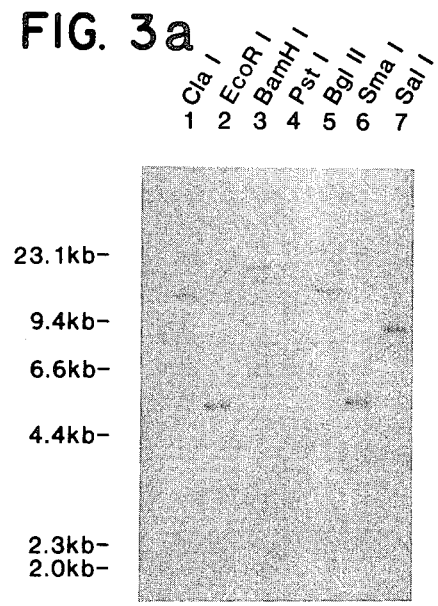
FIG. 3b
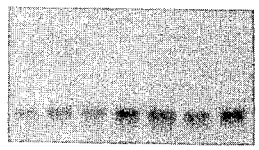
FIG. 3c
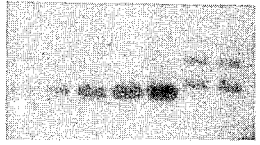

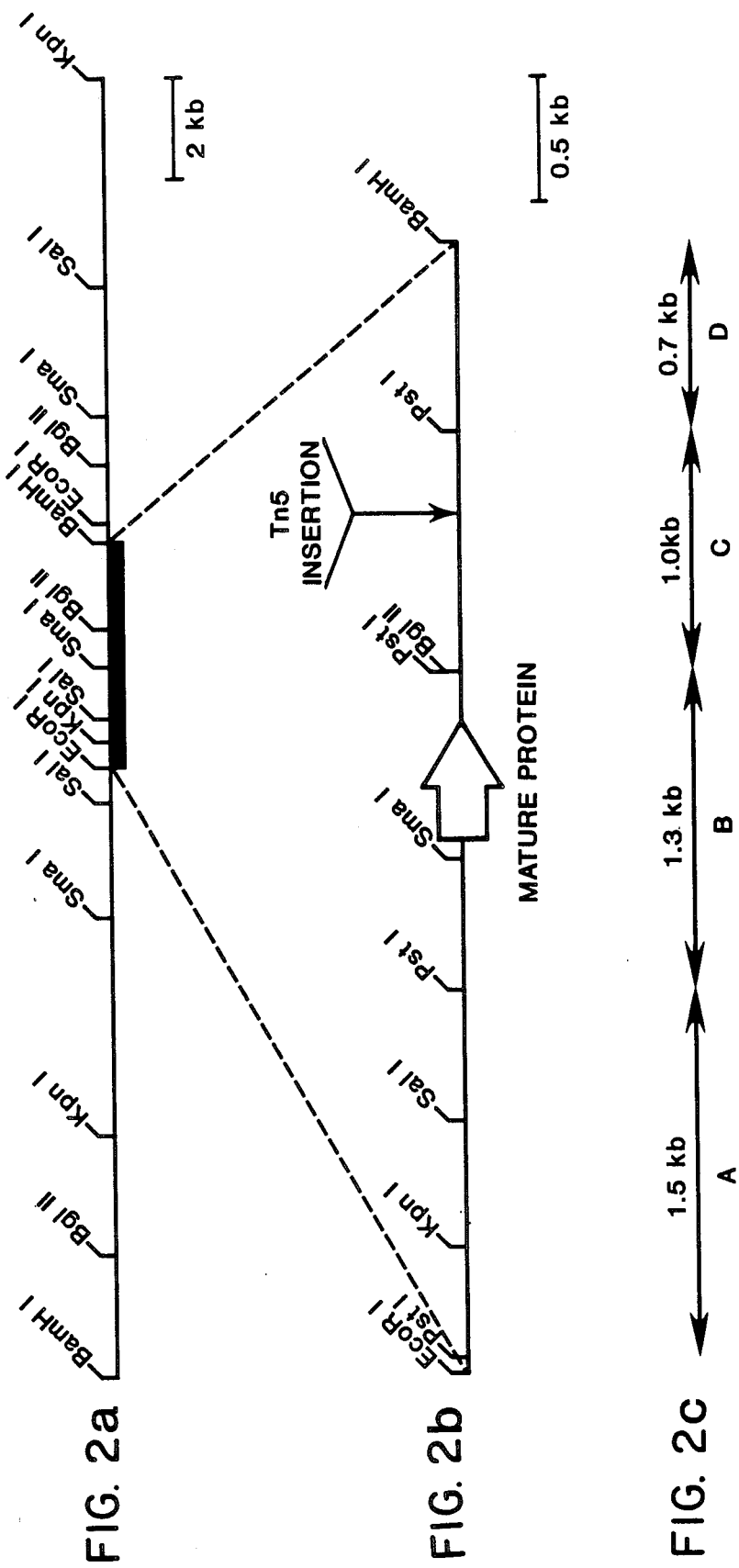

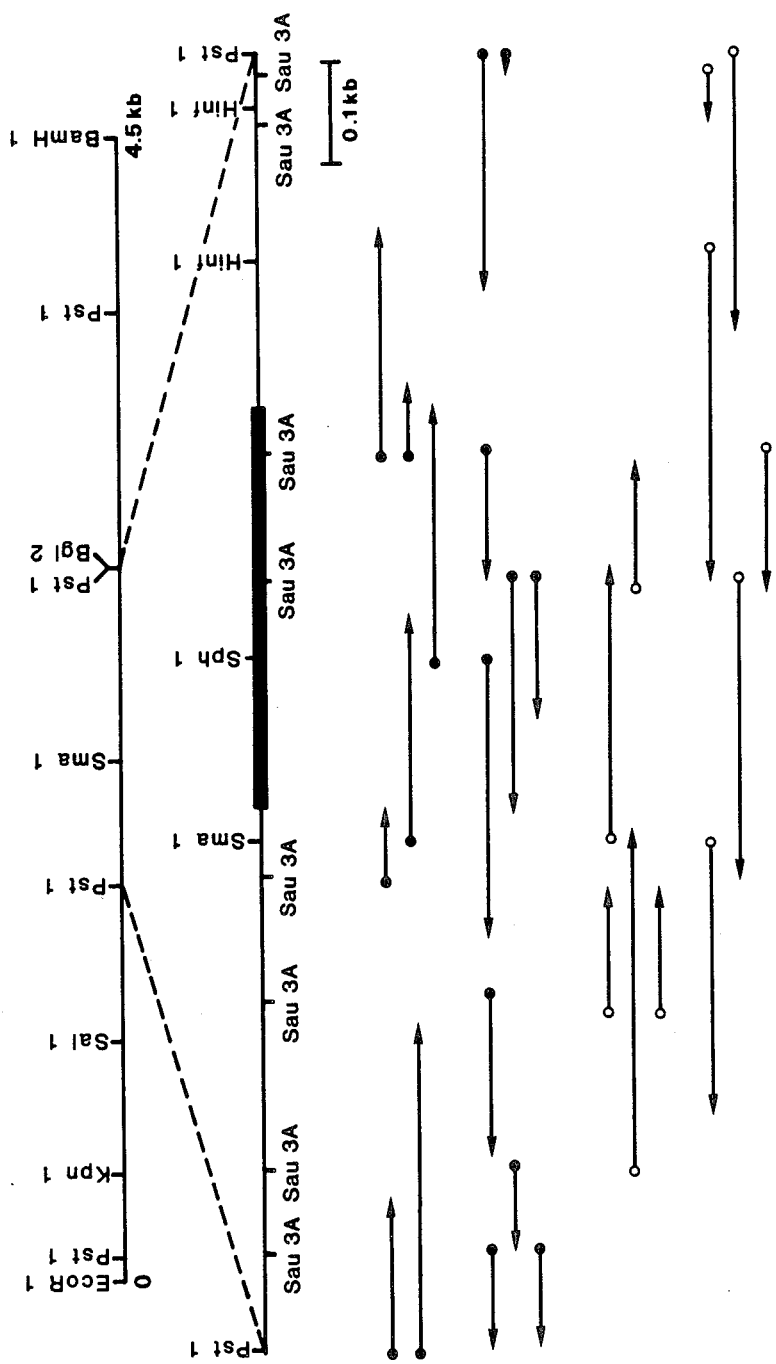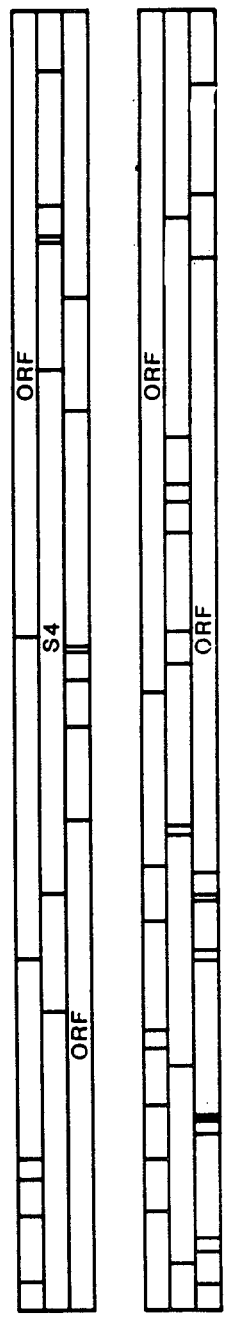
FIG. 5a  FIG. 5b  FIG. 5c  FIG. 5d

PERTUSSIS TOXIN GENE: CLONING AND EXPRESSION OF PROTECTIVE ANTIGEN

BACKGROUND OF THE INVENTION

1. Technical Field

The present invention is related to molecular cloning of pertussis toxin genes capable of expressing an antigen peptide protective against pertussis. More particularly, the present invention is related to a bacterial plasmid pPTX42 encoding pertussis toxin.

2. State of The Art

Pertussis toxin is one of the various toxic components produced by virulent *Bordetella pertussis,* the microorganism that causes whooping cough. A wide variety of biological activities such as histamine sensitization, insulin secretion, lymphocytosis promoting and immunopotentiating effects can be attributed to this toxin. In addition to these activities, the toxin provides protection to mice when challenged intracerebrally or by aerosol. Pertussis toxin is, therefore, an important constituent in the vaccine against whooping cough and is included as a component in such vaccines.

However, while this toxin is one of the major protective antigens against whooping cough, it is also associated with a variety of pathophysiological activities and is believed to be the major cause of harmful side effects associated with the present pertussis vaccine. In most recipients these side effects are limited to local reactions, but in rare cases neurological damage and death does occur (Baraff et al., 1979 in Third International Symposium on Pertussis. U.S. HEW publication No. NIH-79-1830). Thus a need to produce a new generation of vaccine against whooping cough is evident.

SUMMARY OF THE INVENTION

It is, therefore, an object of the present invention to clone the gene(s) responsible for expression of pertussis toxin.

It is a further object of the present invention to isolate at least a part of the pertussis toxin genome and determine the nucleotide sequence and genetic organization thereof.

It is yet another object of the present invention to characterize the toxin polypeptide encoded by the cloned gene(s), at least in terms of the aminoacid sequence thereof.

Other objects and advantages of the present invention will become evident upon a reading of the detailed description of the invention presented herein.

BRIEF DESCRIPTION OF DRAWINGS

These and other objects, features and many of the attendant advantages of the invention will be better understood upon a reading of the following detailed description when considered in connection with the accompanying drawings wherein:

FIG. 1 shows SDS-electrophoresis of the products of HPLC separation of pertussis toxin. Lanes 1 and 12 contain 5 μg and 10 μg, respectively, of unfractionated pertussis toxin. Lanes 2 through 11 contain 100 μl aliquots of elution fractions 19 through 28, respectively. The molecular weights of the subunits are indicated;

FIG. 2 shows restriction map of the cloned 4.5 kb EcoRI/BamHI *B. pertussis* DNA fragment and genomic DNA in the region of the pertussis toxin subunit gene. (a) Restriction map of a 26 kb region of *B. pertussis* genomic DNA containing pertussis toxin genes. (b) Restriction map of the 4.5 kb EcoRI/BamHI insert from pPTX42. The arrow indicates the start and translation direction of the mature toxin subunit. The location of the Tn5 DNA insertion in mutant strains BP356 and BP357 is shown. (c) PstI fragment derived from the insert shown in panel b;

FIG. 3 shows Southern blot analysis of *B. pertussis* genomic DNA with cloned DNA probes. (a) Total genomic DNA from strain 3779 was digested with various restriction enzymes as indicated on the figure, and analyzed by Southern blot using nick translated PstI fragment B of pPTX42 (see FIG. 2*c*). (b) Between 24 μg and 60 μg of genomic DNA from strains 3779, Sakairi (pertussis toxin−, Tn5−), BP347 (non-virulent, Tn5+), BP349 (hemolysin−, Tn5+), BP353 (filamentous hemagglutinin−, Tn5+), Bp356 and BP357 (both pertussis toxin−, Tn5+) (15) (lanes 1 through 7, respectively) were digested with PstI and analyzed by Southern blot using nick translated PstI fragment B as the probe. (c) The same as panel b excet PstI fragment C was used as the probe;

FIG. 4 shows the physical map and genetic organization of the Pertussis Toxin Gene. (a) Restriction map of the 4.5 kb EcoRI/BamHI fragment from pPTX42 containing the pertussis toxin gene cloned from *B. pertussis* strain 3779 (12). The arrow indicates the position of the Tn5 DNA insertion in pertussis toxin negative Tn5-induced mutant strains BP356 and BP357 (24). (b) Open reading frames in the forward direction. (c) Open reading frames in the backward direction. The vertical lines indicate termination codons. (d) Organizational map of the pertussis toxin gene. The arrows show the translational direction and length of the protein coding regions for the individual subunits. The hatched boxes represent the signal peptides. The solid bars in S1 represent the regions homologous to the A subunits in cholera and *E. coli* heat labile toxins; and FIG. 5 shows the physical map of the pertussis toxin S4 subunit gene. (a) Restriction map of the 4.5 kilobase pair (kb) EcoRI/BamHI fragment inserted into pMC1403. (b) Detailed restriction map and sequencing strategy of the PstI fragment B containing the S4 subunit gene. Only the restriction sites used for subcloning prior to sequencing are shown. Closed circled arrows show the sequencing strategy using dideoxy chain termination and open circled arrows show the sequencing strategy using base-specific chemical cleavage. The arrows show the direction and the length of the sequence determination. The heavy black line represents the S4 coding region. (c) Open reading frames in the three forward directions. (d) Open reading frames in the three backward directions. The vertical lines indicate termination codons.

DETAILED DESCRIPTION OF INVENTION

The above objects and advantages of the present invention are achieved by molecular cloning of pertussis toxin genes. The cloning of the gene provides means for genetic manipulation thereof and for producing new generation of substantially pure and isolated form of antigenic peptides (toxins) for the synthesis of new generation of vaccine against pertussis. Of course, such manipulation of the pertussis toxin gene and the creation of new, manipulated toxins retaining antigenicity against pertussis but being devoid of undesirable side effects was not heretofore possible. The present invention is the first to clone the pertussis toxin gene in an expression vector, to map its nucleotide sequence and to disclose the finger print of the polypeptide encoded by said gene(s).

Any vector wherein the gene can be cloned by recombination of genetic material and which will express the cloned gene can be used, such as bacterial (e.g. λgt11), yeast (e.g. PGPD-1), Viral (e.g. PGS20 or pMM4), and the like. A preferred vector is the microorganism, E. coli wherein the pertussis gene has been cloned in the plasmid thereof.

Although any similar or equivalent methods and materials could be used in the practice or testing of the present invention, the preferred methods and materials are now described. All scientific and/or technical terms used herein have the same meaning as generally understood by one of ordinary skill in the art to which the invention belongs. All references cited hereunder are incorporated herein by reference.

MATERIALS AND METHODS

Materials. Restriction enzymes were purchased from Bethesda Research Laboratories (BRL) or International Biotechnologies, Inc. and used under conditions recommended by the suppliers. T4 DNA ligase, M13mp19 RF vector, isopropylthio-β-galactoside (IPTG), 5-bromo-4-chloro-3-indolyl-β- D- galactoside (X-Gal), the 17-bp universal primer, Klenow fragment (Lyphozyme®) and $T_4$ polynucleotide kinase were purchased from BRL. Calf intestine phosphatase was obtained from Boehringer Mannheim, nucleotides from PL-Biochemicals and base modifying chemicals from Kodak (dimethylsulfate, hydrazine and piperidine) and EM Science (formic acid). Plasmid pMC1403 and *E. coli* strain JM101 (supE, thi, Δ(lac-proAB), [F′, traD36, proAB, lacI Z ΔM15]) were obtained from Dr. Francis Nano (Rocky Mountain Laboratories, Hamilton, Montana 59840) Elutip-d® columns came from Schleicher and Schuell and low melting point agarose (LMP Agarose®) from BRL. Radiochemicals were supplied by ICN Radiochemicals (crude [$\gamma$-$^{32}$P]ATP, 7000 Ci/mmol) and NEN Research Products ([$\alpha$-$^{32}$P]dGTP, 800 Ci/mmole). *B. pertussis* strain 3779 was obtained from Dr. John J. Munoz, Rocky Mountain Laboratories, Hamilton, Mont. 59840. This strain is also known as 3779 BL2S4 and is commonly available.

Purification of Pertussis Toxin Subunits: Pertussis toxin from *B. Pertussis* strain 3779 was prepared by the method of Munoz et al, Cell Immunol. 83:92-100, 1984. Five mg of the toxin was resuspended in trifluoroacetic acid and fractionated by high pressure liquid chromatography, HPLC, using a 1×25 cm Vydac C-4 preparative column. The sample was injected in 50% trifluoroacetic acid and eluted at 4 ml/min over 30 min with a linear gradient of 25% to 100% acetonitrile solution containing 66% acetonitrile and 33% isopropyl alcohol. All solutions contained 0.1% trifluoroacetic acid. Elution was monitored at 220 nm and two ml fractions collected. Aliquots of selected fractions were dried by evaporation, resuspended in gel loading buffer containing 2-mercaptoethanol and analyzed by sodium dodecylsulphate polyacrylamide gel electrophoresis, SDS-PAGE, on a 12% gel.

Protein and DNA Sequencing: The polypeptide from HPLC fraction 21 (FIG. 1, lane 4) was sequenced using a Beckman 890C automated protein sequenator according to the methods described by Howard et al, Mol. Biochem. Parasit. 12:237-246, 1984. DNA was sequenced from the SmaI site (see FIG. 2*b*) by the Maxam and Gilbert technique as described in Methods in Enzymol. 65:499-560, 1980.

Isolation of Pertussis Toxin Genes: Chromosomal DNA was prepared from *B. pertussis* strain 3779 following the procedure described by Hull et al., Infec. Immunol. 33:933, 1981. The DNA was digested with both endonucleases EcoRI and BamHI and ligated into the same sites in the polylinker of pMC1403 as described by *Casadaban et al.* J. Bacteriol. 143:971-980, 1983; *Maniatis et al,* Molecular Cloning: A Laboratory Manual, 1982. The conditions for ligation were: 60 ng of vector DNA and 40 ng of insert DNA incubated with 1.5 units of T4 DNA ligase (BRL) and 1 mM ATP at 15° C. for 20h. E. coli JM109 cells were transformed with the recombinant plasmid in accordance with the procedure of Hanahan, J. Mol. Biol. 166:557-580, 1983 and clones containing the toxin gene identified by colony hybridization at 37° C. using a $^{32}$P-labeled 17-base mixed oligonucleotide probe 21D3 following the procedure of Woods, Focus 6:1-3, 1984. The probe was synthesized on a SAM-1 DNA synthesizer (Biosearch, San Rafael, Calif.) and consisted of the 32 possible oligonucleotides coding for 6 consecutive amino acids of the pertussis toxin subunit (Table 1). The probe was purified from a 20% urea-acrylamide gel and 5′-end labeled using 0.2 mCi of (gamma$^{32}$P)ATP (ICN, crude, 7000 Ci/mmol) and 1 unit of $T_4$ polynucleotide kinase (BRL) per 10 μl of reaction mixture in 50 mM Tris-HCl (pH 7.4) 5 mM DTT, 10 mM $MgCl_2$. The labeled oligonucleotides were purified by binding to a DEAE-cellulose column (DE52, Whatman) in 10 mM Tris-HCl (pH 7.4), 1 mM EDTA (TE) and eluted with 1.0 M NaCl in TE. Ten positive clones were isolated and purified. Plasmid DNA from these clones were extracted according to the procedure of Maniatis et al, Molecular Cloning: A Laboratory Manual, 1982, digested with routine restriction endonucleases (BRL), and then analyzed by 0.8% agarose gel electrophoresis in TBE (10 mM Trisborate pH 8.0, 1 mM EDTA). Southern blot analysis using the $^{32}$P-labeled oligonucleotide 21D3 as the probe showed that all 10 clones contained an identical insert of *B. pertussis* DNA. One clone was used for further analysis by Southern blots (FIG. 3) and for DNA sequencing.

Southern Blot Analyses: Extracted DNA as described supra, was digested and separated by electrophoresis using either 0.7% or 1.2% agarose gels in 40 mM Tris-acetate pH 8.3, 1 mM EDTA for 17 h at 30 V. The DNA was then blotted onto nitrocellulose in 20X SSPE, sodium chloride, sodium phosphate EDTA buffer, pH 7.4, in accordance with Maniatis et al., supra, and baked at 80° C. in a vacuum oven for 2 h. Filters were prehybridized at 68° C. for 4 h in 6X SSPE, 0.5% SDS, 5X modified Denhardt's (0.1% Ficoll 400, 0.1% bovine serum albumin, 0.1% polyvinylpyrrolidone and 0.3X SSPE) and 100 μg/ml denatured herring sperm DNA. The hybridization buffer was the same as the prehybridization buffer, except EDTA was added to a final concentration of 10 mM. PstI fragments A, B, C and D were isolated by 0.8% low-melting point agarose gel electrophoresis, purified on Elutip-d columns (Schleicher and Schuell) and nick translated (BRL) using (alpha$^{32}$P)CTP (800 Ci/mmol, NEN Research Products). The nick translated probes were hybridized at a concentration of about 1 μCi/ml for 48 h at 68° C. Filters were then washed in 2X SSPE and 0.5% SDS at room (22°-25° C.) temperature for 5 min, then in 2X SSPE and 0.1% SDS at room temperature for 15 min, and finally in 0.1X SSPE and 0.5% SDS at 68° C. for 2 h. The washed filters were air dried and exposed to X-ray film using a Lightning-Plus intensifying screen following standard techniques.

Isolation and cloning of S4 subunit gene: As mentioned above, purified pertussis toxin from *B. pertussis* strain 3779 was fractionated by high pressure liquid chromatography (HPLC). One fraction (Fr21) contained a polypeptide which comigrated as a major band with subunit S4 on SDS-PAGE (FIG. 1, lane 4). Although complete separation was not achieved, the major portion of the other toxin subunits were recovered in other HPLC fractions, i.e., S2 in Fr22, S1 and S5 in Fr23, and S3 in Fr24 (FIG. 1). The amino acid sequence of the first 30 NH$_2$-terminal residues of the protein in fraction 21 was determined and is shown in Table 1.

cleotide probe 21D3. The plasmid DNA of 10 positive colonies was examined by restriction enzyme and Southern blot analyses. All 10 colonies contained a recombinant plasmid with an identical 4.5 kb EcoRI/-BamHI pertussis DNA insert. One of these clones, identified as pPTX42, was selected for further characterization. A restriction map of the insert DNA was prepared and is shown in FIG. 2b; Southern blot analysis indicated that the oligonucleotide probe 21D3 hybridized to only the 0.8 kb SmaI/PstI fragment.

A deposit of said pPTX42 clone has been made in American Type Culture Collection, Rockville, MD under the accession No. 67046. This culture will continue to be maintained for at least 30 years after a patent issues and will be available to the public without restriction, of course, in accordance with the provisions of the

TABLE 1

Protein and DNA Sequences of Pertussis Toxin Subunit, Oligonucleotide Probe and Homologous Genomic DNA Clone

```
DNA sequence:            SmaI                                              f-Met
Predicted amino acid sequence: |C CCG GG| A CAG GGC GGC GCC CGG CGG TCG CGC |GTG| CGC GCC CTG—
                                  Pro Gly  Gln Gly Gly Ala Arg Arg Ser Arg  Val  Arg Ala Leu—
                                      −30                                        −20 f-Met                                    f-Met
                 GCG TGG |TTG| CTG GCA TCC GGC GCG |ATG| ACG CAT CTT TCC CCC GCC CTG—
                 Ala Trp  Leu  Leu Ala Ser Gly Ala  Met  Thr His Leu Ser Pro Ala Leu—
                                                −10

Mature protein sequence:  GCC GAC GTT CCT TAT GTG CTG GTG AAG ACC AAT ATG GTG GTC ACC AGC—
                          Ala* Asp Val Pro Tyr Val Leu Val Lys Thr Asn Met Val Val Thr Ser—

H₂N—Asp Val Pro Tyr Val Leu Val Lys Thr Asn Met Val Val Thr (?)—
                              1                                          10 probe 21D3
                                 |ATG AAP CCN TAY GAP GT|
                          GTA GCC ATG AAG CCG TAT GAA GTC ACC CCG ACG CGC ATG CTG GTC—
                          Val Ala Met Lys Pro Tyr Glu Val Thr Pro Thr Arg Met Leu Val—

Val Ala Met Lys Pro Tyr Glu Val (Val) Pro (Pro) Arg Met Leu Val—
                                        20                                          30
```

The S4 H$_2$N—terminal amino acid sequence determined using the automated protein sequenator is shown in blocks as the mature protein sequence. Residues that were questionable in the sequence are indicated by brackets. The DNA and predicted amino acid sequences are shown. Possible initiation codons are indicated by f-Met. A putative proteolytic cleavage site is indicated by *. The oligonucleotide probe sequence is shown in the block labeled probe 21D3. The abbreviations used are: P = G or A; Y = T or C; N = A, C, G or T.

Based on the protein sequence shown in Table 1, a mixed oligonucleotide probe representing a region of six consecutive amino acids with the least redundancy of the genetic code was synthesized. In this mixture of oligonucleotides, identified as probe 21D3, approximately 1 out of 32 molecules corresponds to the actual DNA sequence of the pertussis toxin gene (Table 1). This mixed oligonucleotide probe was used to screen a DNA clone bank containing restriction fragments of total pertussis chromosomal DNA. The clone bank was prepared by digesting genomic DNA isolated from *B. pertussis* strain 3779 with both EcoRI and BamHI restriction endonucleases. The complete population of restriction fragments was ligated into the EcoRI/-BamHI restriction site of expression vector pMC1403 and the recombinant plasmid used to transform *E. coli* JM109 cells following standard procedures well known in the art. It is noted that although *E. coli* is the preferred organism, other cloning vectors well known in the art, could, of course, be alternatively used.

Approximately 20,000 colonies were screened by colony hybridization using the $^{32}$P-end labeled oligonulaw.

Sequencing of the H$_2$N-terminal region for S4: The 0.8 kb fragment was isolated by agarose gel electrophoresis and sequenced using the Maxam and Gilbert technique, supra. The DNA sequence was translated into an amino acid sequence and a portion of that sequence is compared in Table 1 to the NH$_2$-terminal 30 amino acids of the pertussis toxin subunit and the oligonucleotide probe 21D3 sequence. Out of the sequence of 30 amino acid residues determined using the automated sequenator, only 2 do not correspond to the amino acid sequence deduced from the DNA sequence i.e., residues 24 and 26 are questionable because they repeat the amino acid in front of them and they are located near the end of the analyzed sequence. Amino acid 15 could not be determined. The rest of the deduced amino acid sequence perfectly matches the original protein sequence. The oligonucleotide probe sequence also perfectly matches the cloned DNA sequence. These results indicate that at least one of the pertussis toxin subunit genes has been cloned.

Examination of the DNA sequence indicates that a precursor protein, perhaps containing a leader sequence may exist (Table 1). In fact, the NH$_2$-terminal aspartic acid of the mature protein is not immediately preceded by one of the known initiation codons, i.e., ATG, GTG, TTG, or ATT, but by GCC coding for alanine, an amino acid that often occurs at the cleavage site of a signal peptide. A proline is found at amino acid position −4, which is also consistent with cleavage sites in other known sequences where this amino acid is usually present within six residues of the cleavage site. Possible translation initiation sites in the same reading frame as the mature protein and upstream of the NH$_2$-terminal aspartic acid are: ATG at position −9, TTG at −15, and GTG at −21; however, none of these are preceded by a Shine/Dalgarno ribosomal binding site (Nature., London, 254:34-38, 1975) and only GTG at −21 is immediately followed by a basic amino acid (arginine) preceding a hydrophobic region, characteristic of bacterial signal sequences. Using the DNA sequence data and primer extension to sequence the mRNA, the actual initiation site could also be determined.

Physical mapping of the S4 gene on the bacterial chromosome: The 1.3 kb PstI fragment B containing at least part of the pertussis toxin gene was used as a probe to physically map the location of this gene on the *B. pertussis* genome (FIG. 2). FIG. 3a shows a Southern blot analysis of total *B. pertussis* DNA digested with a variety of six base pair-specific restriction enzymes and probed with the 1.3 kb PstI fragment B isolated from pPTX42. Each restriction digest yielded only one DNA band which hybridized with the probe. Since the 1.3 kb PstI fragment B contains a SmaI site, two bands would be expected from a SmaI digest of genomic DNA unless the SmaI fragments were similar in size. Further analysis indicated that the single band seen in the SmaI digest is actually a doublet of two similar size DNA fragments. In this particular gel, fragments of 1.3 kb and smaller migrated off the gel during electrophoresis and thus could not be detected, however, in other Southern blots in which no fragment was run off the gel, only one band was found for each restriction enzyme. These results indicate that the gene encoded by the PstI fragment B occurs only once in the genome. Using the data from these experiments and similar studies using the 1.5 kb PstI fragment A and the 0.7 kb PstI/BamHI fragment D from the cloned 4.5 kb EcoRI/BamHI fragment, a partial restriction map of a 26 kb region of the pertussis genome as shown in FIG. 2a was obtained. This method allowed to locate the first restriction site of a particular endonuclease on either side of the 4.5 kb EcoRI/BamHI fragment. This information i useful in deciphering the genetic arrangement of the toxin genes and for the cloning of larger DNA fragments of pertussis toxin.

Relationship of the S4 gene and Tn5-insertions: Weiss et al, Infect. Immun. 42:33-41, 1983, have developed several important Tn5-induced *B. pertussis* mutants deficient in different virulence factors, i.e., pertussis toxin, hemolysin, and filamentous hemagglutinin (Infect. Immun. 43:263-269, 1984; J. Bacteriol. 153:304-309, 1983). To investigate the physical relationship between the Tn5 DNA insertion and the pertussis toxin subunit gene, genomic DNA from these mutants and strain 3779 by Southern blots using various restriction fragments of the cloned 4.5 kb EcoRI/BamHI DNA fragment as probes were analyzed. In one set of experiments, blots of genomic PstI fragments were separately probed with cloned PstI fragments A, B, C, and D (FIG. 2c). The PstI fragments from the mutants and strain 3779 which hybridized with the cloned PstI fragments A, B, and D were exactly the same size; the blot probed with PstI fragment B is shown in FIG. 3b. However, when the PstI fragment C was used as a probe, the genomic DNA from mutant strains BP356 and BP357 showed a clear difference in the size of the PstI fragments that hybridized as compared to strain 3779 and the other mutant strains (FIG. 3c, lanes 6 and 7). These results indicate that this fragment contains the site of the Tn5 insertion. As expected, two labeled fragments were found, since the Tn5 DNA insert has two symmetrical PstI sites. Other Southern blots (not shown) in which genomic BglII and SmaI fragments were hybridized with the 4.5 kb EcoRI/BamHI cloned probe, and the data from FIG. 3c, clearly show that the Tn5 DNA was inserted 1.3 kb downstream from the start of the mature pertussis toxin S4 subunit in the two mutant strains that were characterized as pertussis toxin negative phenotypes, i.e., BP356 and BP357 (FIG. 2b). This insertion is beyond the termination codon for the S4 subunit (11.7 kD). Examination of these toxin negative mutants by Western blots using monoclonal antibodies for individual subunits indicate that the Tn5 DNA is not inserted in the subunit structural genes for S1 or S2 (unpublished results). The pertussis toxin negative phenotype of strains BP356 and BP357 can be explained by either of two nonexclusive mechanisms. The Tn5 DNA may be inserted into the coding regions of either S3, S5, or perhaps another gene required for toxin assembly or transport. Alternatively, the Tn5 insertion could disrupt the expression of essential downstream cistrons in a polycistronic operon. Similar Southern blot analyses of genomic BamHI and EcoRI fragments indicate that none of the other virulence factor genes represented by the other Tn5-insertion mutants, are located within the 17kb region defined by the first BamHI and the second EcoRI sites as shown in FIG. 2a.

Nucleotide Sequence

Having described the identification, isolation, and construction of recombinant plasmid pPTX42, containing pertussis toxin genes, the insert DNA from this plasmid, i.e., the 4.5 kb EcoRI/BamHI fragment shown in FIG. 4a, was digested with various restriction enzymes and subcloned by standard procedures (Maniatis et al., supra) using the cloning vectors M13 mp18 and M13 mp19 and *E. coli* strain JM101 as described by Messing, Methods Enzymol. 101:20-78, 1983. Both strands of the DNA were sequenced using either the Maxam and Gilbert base-specific chemical cleavage method, supra, or the dideoxy chain termination method of Sanger et al., PNAS, 74:5463-5467, 1977, with the universal 17-base primer, or both. The DNA sequence and the derived amino acid sequence were analyzed using MicroGenie ® computer software.

Because of the high C+G content of *B. pertussis* DNA, it was necessary to use both of the above mentioned methods with a combination of 8% and 20% polyacrylamide-8 M urea gels for sequence analysis. Each nucleotide has been sequenced in both directions an average of 4.13 times. The final consensus sequence of the sense strand is shown in Table 2. It is noted that the sequence of the S4 subunit gene has been included in this table for completeness since this sequence lies in the middle of the structural gene sequence presented in Table 2. The entire sequence contains about 62.2% C+G with about 19.6% A, 33.8% C, 28.4% G and 18.2% T in the sense strand, wherein A, T, C and G represent the nucleotides adenine, thymine, cytosine and guanine, respectively.

TABLE 2

Complete Nucleotide Sequence of Pertussis Toxin Gene

```
EcoRI
GAATTC GTCGCCTCGCCCTGGTTCGCCGTCATGGCCCCCAAGGGAACCGACCCCAAGATA
                                          100
ATCGTCCTGCTCAACCGCCACATCAACGAGGCGCTGCAGTCCAAGGCGGTCGTCGAGGCC

TTTGCCGCCCAAGGCGCCACGCCGGTCATCGCCACGCCGGATCAGACCCGCGGCTTCATC
                    200
GCAGACGAGATCCAGCGCTGGGCCGGCGTCGTGCGCGAAACCGGCGCCAAGCTGAAGTAG
                                                          300
CAGCGCAGCCCTCCAACGCGCCATCCCCGTCCGGCCGGCACCATCCCGCATACGTGTTGG

CAACCGCCAACGCGCATGCGTGCAGATTCGTCGTACAAAACCCTCGATTCTTCCGTACAT
                                        400
CCCGCTACTGCAATCCAACACGGCATGAACGCTCCTTCGGCGCAAAGTCGCGCGATGGTA
                           -35                              -10
CCGGTCACCGTCCGGACCGTG CTGACC CCCCTGCCATGGTGTGATCCG TAAAATA GGCAC
                     500           S1
CAT CAAAACGCAGAGGGGAAGACGGGATGCGTTGCACTCGGGCAATTCGCCAAACCGCAA
                                fM  R  C  T  R  A  I  R  Q  T  A
                                                          600
GAACAGGCTGGCTGACGTGGCTGGCGATTCTTGCCGTCACGGCGCCCGTGACTTCGCCGG
R  T  G  W  L  T  W  L  A  I  L  A  V  T  A  P  V  T  S  P

CATGGGCCGACGATCCTCCCGCCACCGTATACCGCTATGACTCCCGCCCGCCGGAGGACG
A  W  A *D  D  P  P  A  T  V  Y  R  Y  D  S  R  P  P  E  D
                                          700
TTTTCCAGAACGGATTCACGGCGTGGGGAAACAACGACAATGTGCTCGACCATCTGACCG
V  F  Q  N  G  F  T  A  W  G  N  N  D  N  V  L  D  H  L  T

GACGTTCCTGCCAGGTCGGCAGCAGCAACAGCGCTTTCGTCTCCACCAGCAGCAGCCGGC
G  R  S  C  Q  V  G  S  S  N  S  A  F  V  S  T  S  S  S  R
                     800
GCTATACCGAGGTCTATCTCGAACATCGCATGCAGGAAGCGGTCGAGGCCGAACGCGCCG
R  Y  T  E  V  Y  L  E  H  R  M  Q  E  A  V  E  A  E  R  A
                                                          900
GCAGGGGCACCGGCCACTTCATCGGCTACATCTACGAAGTCCGCGCCGACAACAATTTCT
G  R  G  T  G  H  F  I  G  Y  I  Y  E  V  R  A  D  N  N  F

ACGGCGCCGCCAGCTCGTACTTCGAATACGTCGACACTTATGGCGACAATGCCGGCCGTA
Y  G  A  A  S  S  Y  F  E  Y  V  D  T  Y  G  D  N  A  G  R
                                          1000
TCCTCGCCGGCGCGCTGGCCACCTACCAGAGCGAATATCTGGCACACCGGCGCATTCCGC
I  L  A  G  A  L  A  T  Y  Q  S  E  Y  L  A  H  R  R  I  P

CCGAAAACATCCGCAGGGTAACGCGGGTCTATCACAACGGCATCACCGGCGAGACCACGA
P  E  N  I  R  R  V  T  R  V  Y  H  N  G  I  T  G  E  T  T
                     1100
CCACGGAGTATTCCAACGCTCGCTACGTCAGCCAGCAGACTCGCGCCAATCCAACCCCT
T  T  E  Y  S  N  A  R  Y  V  S  Q  Q  T  R  A  N  P N  P
                                                          1200
ACACATCGCGAAGGTCCGTAGCGTCGATCGTCGGCACATTGGTGCATGGCGCCGGTGATA
Y  T  S  R  R  S  V  A  S  I  V  G  T  L  V  H  G  A  G  D

GCGCTTGCATGGCGCGGCAGGCCGAAAGCTCCGAGGCCATGGCAGCCTGGTCCGAACGCG
S  A  C  M  A  R  Q  A  E  S  S  E  A  M  A  A  W  S  E  R
                                          1300
CCGGCGAGGCGATGGTTCTCGTGTACTACGAAAGCATCGCGTATTCGTTCTAGACCTGGC
A  G  E  A  M  V  L  V  Y  Y  E  S  I  A  Y  S  F  U
                                         S2
CCAGCCCCGCCCAACTCCGGTAATTGAACAGCATGCCGATCGACCGCAAGACGCTCTGCC
                                   f M  P  I  D  R  K  T  L  C
                    1400
ATCTCCTGTCCGTTCTGCCGTTGGCCCTCCTCGGATCTCACGTGGCGCGGGCCTCCACGC
H  L  L  S  V  L  P  L  A  L  L  G  S  H  V  A  R  A *S  T
                                                          1500
CAGGCATCGTCATTCCGCCGCAGGAACAGATTACCCAGCATGGCAGCCCCTATGGACGCT
P  G  I  V  I  P  P  Q  E  Q  I  T  Q  H  G  S  P  Y  G  R
```

TABLE 2-continued
Complete Nucleotide Sequence of Pertussis Toxin Gene

```
GCGCGAACAAGACCCGTGCCCTGACCGTGGCGGAATTGCGCGGCAGCGGCGATCTGCAGG
 C   A   N   K   T   R   A   L   T   V   A   E   L   R   G   S   G   D   L   Q
                                          1600
AGTACCTGCGTCATGTGACGCGCGGCTGGTCAATATTTGCGCTCTACGATGGCACCTATC
 E   Y   L   R   H   V   T   R   G   W   S   I   F   A   L   Y   D   G   T   Y

TCGGCGGCGAATATGGCGGCGTGATCAAGGACGGAACACCCGGCGGCGCATTCGACCTGA
 L   G   G   E   Y   G   G   V   I   K   D   G   T   P   G   G   A   F   D   L
                     1700
AAACGACGTTCTGCATCATGACCACGCGCAATACGGGTCAACCCGCAACGGATCACTACT
 K   T   T   F   C   I   M   T   T   R   N   T   G   Q   P   A   T   D   H   Y
                                                              1800
ACAGCAACGTCACCGCCACTCGCCTGCTCTCCAGCACCAACAGCAGGCTATGCGCGGTCT
 Y   S   N   V   T   A   T   R   L   L   S   S   T   N   S   R   L   C   A   V

TCGTCAGAAGCGGGCAACCGGTCATTGGCGCCTGCACCAGCCCGTATGACGGCAAGTACT
 F   V   R   S   G   Q   P   V   I   G   A   C   T   S   P   Y   D   G   K   Y
                                          1900
GGAGCATGTACAGCCGGCTGCGGAAAATGCTTTACCTGATCTACGTGGCCGGCATCTCCG
 W   S   M   Y   S   R   L   R   K   M   L   Y   L   I   Y   V   A   G   I   S

TACGCGTCCATGTCAGCAAGGAAGAACAGTATTACGACTATGAGGACGCAACGTTCGAGA
 V   R   V   H   V   S   K   E   E   Q   Y   Y   D   Y   E   D   A   T   F   E
                     2000
CTTACGCCCTTACCGGCATCTCCATCTGCAATCCTGGATCATCCTTATGCTGAGACGCTT
 T   Y   A   L   T   G   I   S   I   C   N   P   G   S   S   L   C   U
                                                        S4 ->   2100
CCCCACTCGAACCACCGCCCCGGGACAGGGCGGCGCCCGGCGGTCGCGCGTGCGCGCCCT
                                                       fM   R   A   L

GGCGTGGTTGCTGGCATCCGGCGCGATGACGCATCTTTCCCCCGCCCTGGCCGACGTTCC
   A   W   L   L   A   S   G   A   M   T   H   L   S   P   A   L   A *D   V   P
                                          2200
TTATGTGCTGGTGAAGACCAATATGGTGGTCACCAGCGTAGCCATGAAGCCGTATGAAGT
   Y   V   L   V   K   T   N   M   V   V   T   S   V   A   M   K   P   Y   E   V

CACCCCGACGCGCATGCTGGTCTGCGGCATCGCCGCCAAACTGGGCGCCGCGGCCAGCAG
   T   P   T   R   M   L   V   C   G   I   A   A   K   L   G   A   A   A   S   S
                     2300
CCCGGACGCGCACGTGCCGTTCTGCTTCGGCAAGGATCTCAAGCGTCCCGGCAGCAGTCC
   P   D   A   H   V   P   F   C   F   G   K   D   L   K   R   P   G   S   S   P
                                                              2400
CATGGAAGTCATGTTGCGCGCCGTCTTCATGCAACAACGGCCGCTGCGCATGTTTCTGGG
   M   E   V   M   L   R   A   V   F   M   Q   Q   R   P   L   R   M   F   L   G

TCCCAAGCAACTCACTTTCGAAGGCAAGCCCGCGCTCGAACTGATCCGGATGGTCGAATG
   P   K   Q   L   T   F   E   G   K   P   A   L   E   L   I   R   M   V   E   C
                                       S5 ->
CAGCGGCAAGCAGGATTGCCCCTGAAGGCGAACCCCATGCATACCATCGCATCCATCCTG
   S   G   K   Q   D   C   P   U           fM   H   T   I   A   S   I   L

TTGTCCGTGCTCGGCATATACAGCCCGGCTGACGTCGCCGGCTTGCCGACCCATCTGTAC
   L   S   V   L   G   I   Y   S   P   A   D   V *A   G   L   P   T   H   L   Y
                     2600
AAGAACTTCACTGTCCAGGAGCTGGCCTTGAAACTGAAGGGCAAGAATCAGGAGTTCTGC
   K   N   F   T   V   Q   E   L   A   L   K   L   K   G   K   N   Q   E   F   C
                                                              2700
CTGACCGCCTTCATGTCGGGCAGAAGCCTGGTCCGGGCGTGCCTGTCCGACGCGGGACAC
   L   T   A   F   M   S   G   R   S   L   V   R   A   C   L   S   D   A   G   H

GAGCACGACACGTGGTTCGACACCATGCTTGGCTTTGCCATATCCGCGTATGCGCTCAAG
   E   H   D   T   W   F   D   T   M   L   G   F   A   I   S   A   Y   A   L   K
                                                    2800
AGCCGGATCGCGCTGACGGTGGAAGACTCGCCGTATCCCGGGCACTCCCGGCGATCTGCTC
   S   R   I   A   L   T   V   E   D   S   P   Y   P   G   T   P   G   D   L   L

GAACTGCAGATCTGCCCGCTCAACGGATATTGCGAATGAACCCTTCCGGAGGTTTCGACG
   E   L   Q   I   C   P   L   N   G   Y   C   E   U
                     2900
TTTCCGCGCAATCCGCTTGAGACGATCTTCCGCCCTGGTTCCATTCCGGGAACACCGCAA
 S3 ->                                                       3000
CATGCTGATCAACAACAAGAAGCTGCTTCATCACATTCTGCCCATCCTGGTGCTCGCCCT
fM   L   I   N   N   K   K   L   L   H   H   I   L   P   I   L   V   L   A   L
```

TABLE 2-continued
Complete Nucleotide Sequence of Pertussis Toxin Gene

Figure 4B:
Figure 4C:
Figure 4D:

```
GCTGGGCATGCGCACGGCCCAGGCCGTTGCGCCAGGCATCGTCATCCCGCCGAAGGCACT
  L   G   M   R   T   A   Q   A *V   A   P   G   I   V   I   P   P   K   A   L
                                                 3100
GTTCACCCAACAGGGCGGCGCCTATGGACGCTGCCCGAACGGAACCCGCGCCTTGACCGT
  F   T   Q   Q   G   G   A   Y   G   R   C   P   N   G   T   R   A   L   T   V

GGCCGAACTGCGCGGCAACGCCGAATTGCAGACGTATTTGCGCCAGATAACGCCCGGCTG
  A   E   L   R   G   N   A   E   L   Q   T   Y   L   R   Q   I   T   P   G   W
               3200
GTCCATATACGGTCTCTATGACGGTACGTACCTGGGCCAGGCGTACGGCGGCATCATCAA
  S   I   Y   G   L   Y   D   G   T   Y   L   G   Q   A   Y   G   G   I   I   K
                                                                     3300
GGACGCGCCGCCAGGCGCGGGGTTCATTTATCGCGAAACTTTCTGCATCACGACCATATA
  D   A   P   P   G   A   G   F   I   Y   R   E   T   F   C   I   T   T   I   Y

CAAGACCGGGCAACCGGCTGCGGATCACTACTACAGCAAGGTCACGGCCACGCGCCTGCT
  K   T   G   Q   P   A   A   D   H   Y   Y   S   K   V   T   A   T   R   L   L
                                                 3400
CGCCAGCACCAACAGCAGGCTGTGCGCGGTATTCGTCAGGGACGGGCAATCGGTCATCGG
  A   S   T   N   S   R   L   C   A   V   F   V   R   D   G   Q   S   V   I   G

AGCCTGCGCCAGCCCGTATGAAGGCAGGTACAGAGACATGTACGACGCGCTGCGGCGCCT
  A   C   A   S   P   Y   E   G   R   Y   R   D   M   Y   D   A   L   R   R   L
               3500
GCTGTACATGATCTATATGTCCGGCCTTGCCGTACGCGTCCACGTCAGCAAGGAAGAGCA
  L   Y   M   I   Y   M   S   G   L   A   V   R   V   H   V   S   K   E   E   Q
                                                                     3600
GTATTACGACTACGAGGACGCCACATTCCAGACCTATGCCCTCACCGGCATTTCCCTCTG
  Y   Y   D   Y   E   D   A   T   F   Q   T   Y   A   L   T   G   I   S   L   C

CAACCCGGCAGCGTCGATATGCTGAGCCGCCGGCTCGGATCTGTTCGCCTGTCCATGTTTT
  N   P   A   A   S   I   C   U
                                                 3700
TTCCTTGACGGATACCGCGAATGAATCCCTTGAAAGACTTGAGAGCATCGCTACCGCGCC

TGGCCTTCATGGCAGCCTGCACCCTGTTGTCCGCCACGCTGCCCGACCTCGCCCAGGCCG
               3800
GCGGCGGGCTGCAGCGCTGTCAACCACTTCATGGCGAGCATCGTGGTCGTACTGCCGCGG
                                                                     3900
CGGTCAGTGGCCACGGTGACCATCGCCATAATCTGGGCGGGCTACAAGCTGCTGTTCCGG

CACGCCGATGTGCTGGACGTGGTGCGTGTGGTGCTGGCGGGAGCTGCTGATCGGCGCATC
                                                 4000
GGCCGAAATCGCTCGTTATCTGCTGACCTGAATCCTGGACGTATCGAACATGCGTGATCC

<-----------------                                 -----------
GCTTTTCAAGGGCTGCACCCGGCGCCGCGATGCTGATGGCGTACCCGCCACGGCAGGCCG

---------->    4100
TGTGCAGCCGGCACCATTCCCTGCTGGGCCATCTCGGTTCAGCATCCGCTTTCTGGCCTT
                                                                     4200
GTTTCCCGTGGCATTGCTGGCGATGCGGATCATGATCCGGCGCGATGACCAGCAGTTCCG
  Sau3A
CCT [GATC]
```

The deduced amino acid sequences of the individual subunits are shown in the single letter code below the nucleotide sequence. The proposed signal peptide cleavage sites are indicated by asterisks. The start of the protein coding region for each subunit is indicated by the box and arrow over the initiation codon. Putative ribosomal binding sites are underlined. The promoter-like sequence is shown in the −35 and −10 boxes. Proposed transcriptional start site is indicated by the arrow in the CAT box. Inverted repeats are indicated by the arrows in the flanking regions.

Assignment of the subunit cistrons

The DNA sequence shown in Table 2 was translated in all six reading frames and the reading frames are shown in FIG. 4*b,c*. The open reading frame (ORF) corresponding to the S4 subunit was identified and is shown in FIG. 4*d*. The assignment of the other subunits to their respective ORFs is based on the following lines of evidence: size of ORFs, high coding probability, deduced amino acid composition, predicted molecular weights, ratios of acidic to basic amino acids, amino acid homology to other bacterial toxins, mapping of Tn5-induced mutations, and partial amino acid sequence.

Significant ORFs, long enough to code for any of the five toxin subunits, were analyzed by the statistical TESTCODE algorithm designed to differentiate between real protein coding sequences and fortuitous open reading frames in accordance with Fickett, Nucleic Acids Res. 10:5303, 1982. The amino acid composition of each ORF with a high protein coding probability was calculated, starting from either the predicted amino terminus of the mature proteins or from the first amino acid for the mature protein determined by amino acid sequencing of HPLC purified subunits. These data were then compared with the experimentally-determined compositions of the individual subunits as described by Tamura et al. Biochem. 21:5516, 1982. Based on the similarity of the amino acid compositions shown in Table 3, all five subunits were identified and assigned to the ORF regions shown in FIG. 4d. Table 3 shows that the deduced amino acid composition from all five assigned subunits are in good agreement with the experimentally-determined compositions of Tamura et al supra, with two significant exceptions. First, the S1 subunit contains no lysine residues in the deduced amino acid sequence, whereas 2.2% lysine was experimentally determined. Second, in subunits S2, S3, S4, and 55 the proportion of cysteines were substantially underestimated in the experimentally observed compositions. These discrepancies, as well as the remaining minor differences observed for all subunits, including the previously assigned S4 subunit, can most reasonably be explained by experimental error during amino acid analysis. Similar analyses, in which a DNA-deduced amino acid composition was compared with an experimentally-derived amino acid composition show the same minor differences. The absence of lysine residues in S1 may explain why lysine-specific chemical modification does not affect the biological and enzymatic activities of S1. The amino acid composition of the ORFs (FIG. 4b,c) not assigned to any subunit show no similarity to any of the experimentally-determined amino acid compositions, although some of these ORFs are quite long and have a high coding potential. It is possible that these regions code for other proteins, perhaps involved in the assembly or transport of pertussin toxin.

The experimentally-estimated molecular weight and isoelectric point of the individual subunits were compared to the calculated molecular weight and ratio of acidic to basic amino acids of the putative proteins encoded by the ORFs shown in FIG. 4. As expected for this comparison, Table 3 shows that differences in the ratios reflect corresponding differences in the observed isoelectric points for each subunit, i.e., the higher the acidic content, the lower the isoelectric point. The comparison of the molecular weights also shows good correspondence to the experimentally-determined values, with slight differences for the S1 (less than 10%) and the S5 (about 15%) subunits. These small differences are within acceptable limits for protein molecular weights determined by SDS-PAGE.

TABLE 3

Comparison of the Observed Amino Acid Composition With the Calculated Composition From DNA Sequence for Mature Pertussis Toxin Subunits

| | S1 | | S2 | | S3 | | S4 | | | S5 | |
|---|---|---|---|---|---|---|---|---|---|---|---|
| | | | | | | | Observed values[a] | | Calculated | | |
| | Observed values[a] | Calculated values | Observed values[a] | Calculated values | Observed values[a] | Calculated values | Exp. 1 | Exp. 2 | values | Observed values[a] | Calculated values |
| $Mr^b$ | 28 k | 26.0 k | 23 k | 21.9 k | 22 k | 21.9 k | 11.7 k | — | 12.1 k | 9.3 k | 11.0 k |
| $A/B^c$ | — | 1.3 | — | 0.89 | — | 0.83 | — | — | 0.65 | — | 1.4 |
| $pI^d$ | 5.8 | — | 8.5 | — | 8.8 | — | 10.0 | 10.0 | — | 5.0 | — |
| Ala | 10.6 | 11.5 | 6.5 | 6.0 | 11.7 | 11.1 | 9.4 | 9.8 | 8.2 | 9.8 | 9.0 |
| Arg | 5.9 | 9.0 | 6.2 | 6.0 | 6.1 | 6.5 | 5.1 | 5.4 | 5.5 | 3.3 | 3.0 |
| $Asn^e$ | 9.3 | 5.6 | 6.3 | 2.5 | 6.3 | 2.0 | 5.3 | 5.0 | 0.9 | 8.2 | 3.0 |
| Asp | — | 4.3 | — | 4.0 | — | 4.0 | — | — | 3.6 | — | 5.0 |
| Cys | 1.0 | 0.9 | 1.3 | 3.0 | 1.1 | 3.0 | 0.9 | 0.7 | 3.6 | 1.6 | 4.0 |
| $Gln^f$ | 10.6 | 3.0 | 8.7 | 3.5 | 9.0 | 4.5 | 9.5 | 9.1 | 3.6 | 9.3 | 3.0 |
| Glu | — | 7.3 | — | 4.0 | — | 3.5 | — | — | 4.5 | — | 6.0 |
| Gly | 11.2 | 7.7 | 13.0 | 10.6 | 11.9 | 10.1 | 9.6 | 8.9 | 6.4 | 8.7 | 8.0 |
| His | 1.7 | 2.6 | 2.4 | 2.0 | 1.0 | 1.0 | 0.5 | 0.5 | 0.9 | 3.0 | 3.0 |
| Ile | 3.2 | 3.4 | 4.2 | 5.5 | 5.0 | 6.5 | 2.0 | 1.8 | 1.8 | 3.4 | 3.0 |
| Leu | 5.5 | 3.4 | 7.3 | 7.5 | 8.1 | 8.0 | 8.4 | 8.7 | 9.1 | 13.8 | 15.0 |
| Lys | 2.2 | 0 | 3.4 | 3.0 | 2.7 | 2.5 | 6.9 | 7.6 | 7.3 | 4.7 | 5.0 |
| Met | 1.6 | 1.7 | 1.4 | 1.5 | 1.1 | 1.5 | 5.1 | 4.3 | 7.3 | 1.6 | 2.0 |
| Phe | 3.5 | 3.0 | 3.2 | 2.5 | 3.2 | 2.5 | 3.6 | 4.5 | 4.5 | 4.9 | 5.0 |
| Pro | 4.4 | 3.4 | 4.6 | 4.5 | 5.7 | 5.0 | 9.1 | 9.9 | 10.0 | 5.6 | 5.0 |
| Ser | 10.6 | 9.8 | 8.5 | 8.5 | 6.3 | 5.0 | 8.0 | 7.3 | 5.5 | 6.9 | 6.0 |
| Thr | 7.4 | 7.3 | 10.4 | 10.1 | 8.2 | 8.0 | 5.0 | 5.1 | 4.5 | 6.9 | 7.0 |
| Trp | $ND^g$ | 0.9 | ND | 1.0 | ND | 0.5 | ND | ND | 0 | ND | 1.0 |
| Tyr | 4.6 | 8.1 | 7.6 | 8.0 | 7.9 | 9.5 | 2.2 | 2.0 | 1.8 | 4.3 | 4.0 |
| Val | 6.7 | 7.3 | 4.9 | 6.0 | 4.7 | 5.0 | 9.4 | 9.4 | 10.9 | 4.0 | 3.0 |

[a]Data from Tamava et, al. Biochem 21:5516, 1982.
[b]Mr = molecular weight.
[c]A/B = acid amino acids (Glu + Asp) ÷ basic amino acids (Arg + Lys).
[d]pI = isoelectric pH.
[e]Observed values are Asn + Asp.
[f]Observed values are Gln + Glu.
[g]ND = not determined

TABLE 4

Comparison of Two Homologous Regions in ADP-ribosylating subunits of Pertussis, Cholera, and E. coli Heat Labile Toxins.

Region 1
Pertussis S1 subunit (8) Tyr Arg Tyr Asp Ser Arg Pro Pro (15)
Cholera[a] A subunit (6) Tyr Arg Ala Asp Ser Arg Pro Pro (13)
E. coli[a] HLT A subunit (6) Tyr Arg Ala Asp Ser Arg Pro Pro (13)

Region 2
Pertussis S1 subunit (51) Val Ser Thr Ser Ser Ser Arg Arg (58)
Cholera[a] A subunit (60) Val Ser Thr Ser Ile Ser Leu Arg (67)
E. coli[a] HLT A subunit (60) Val Ser Thr Ser Leu Ser Leu Arg (67)

The numbers in parentheses refer to the amino acid position in the mature proteins.
[a]Data from Yamamoto, et al. FEBS Letter 169:241, 1983. HLT = Heat Labile Toxin.

TABLE 5

Comparison of Codon Usage Between Pertussis Toxin and Strongly and Weakly Expressed E. coli Genes

| | | Pertussis Toxin[a] | | | | | | E. coli[b] | | | | Pertussis Toxin[a] | | | | | | E. coli[b] | |
|---|---|---|---|---|---|---|---|---|---|---|---|---|---|---|---|---|---|---|---|
| | | S1 | S2 | S3 | S4 | S5 | PTX[c] | S[c] | W[c] | | | S1 | S2 | S3 | S4 | S5 | PTX[c] | S[c] | W[c] |
| Ala | GCU | 3 | 0 | 1 | 0 | 1 | 5 | 33 | 17 | Lys | AAA | 0 | 2 | 0 | 1 | 1 | 4 | 49 | 31 |
| | GCC | 17 | 7 | 14 | 9 | 4 | 52 | 9 | 34 | | AAG | 0 | 5 | 7 | 7 | 4 | 24 | 20 | 8 |
| | GCA | 5 | 3 | 2 | 1 | 1 | 12 | 23 | 20 | Met | AUG | 4 | 3 | 4 | 9 | 2 | 22 | 27 | 25 |
| | GCG | 9 | 5 | 8 | 5 | 5 | 33 | 25 | 28 | Phe | UUU | 0 | 1 | 0 | 1 | 1 | 3 | 7 | 29 |
| Arg | CGU | 3 | 2 | 0 | 1 | 0 | 6 | 42 | 19 | | UUC | 7 | 4 | 5 | 4 | 4 | 25 | 22 | 19 |
| | CGC | 12 | 7 | 9 | 4 | 0 | 33 | 19 | 25 | Pro | CCU | 1 | 1 | 0 | 1 | 0 | 3 | 4 | 6 |
| | CGA | 1 | 0 | 0 | 0 | 0 | 1 | 1 | 5 | | CCC | 5 | 3 | 2 | 6 | 1 | 17 | 0.4 | 9 |
| | CGG | 5 | 3 | 1 | 2 | 2 | 13 | 0.2 | 8 | | CCA | 0 | 1 | 2 | 0 | 0 | 3 | 5 | 9 |
| | AGA | 1 | 1 | 1 | 0 | 1 | 4 | 1 | 5 | | CCG | 4 | 6 | 7 | 5 | 5 | 28 | 31 | 19 |
| | AGG | 3 | 1 | 3 | 0 | 0 | 7 | 0.2 | 3 | Ser | UCU | 0 | 1 | 0 | 0 | 0 | 1 | 18 | 7 |
| Asn | AAU | 4 | 2 | 0 | 1 | 1 | 8 | 2 | 19 | | UCC | 7 | 6 | 3 | 2 | 4 | 23 | 17 | 9 |
| | AAC | 9 | 3 | 6 | 0 | 2 | 20 | 30 | 19 | | UCA | 0 | 2 | 0 | 0 | 0 | 2 | 1 | 7 |
| Asp | GAU | 2 | 3 | 1 | 2 | 1 | 9 | 22 | 35 | | UCG | 5 | 0 | 2 | 0 | 2 | 9 | 2 | 12 |
| | GAC | 8 | 6 | 7 | 2 | 5 | 29 | 39 | 20 | | ACU | 0 | 0 | 0 | 1 | 0 | 1 | 2 | 11 |
| Cys | UGU | 0 | 0 | 0 | 0 | 0 | 0 | 2 | 6 | | AGC | 12 | 10 | 5 | 5 | 3 | 36 | 9 | 12 |
| | UGC | 3 | 7 | 6 | 4 | 4 | 25 | 4 | 7 | Thr | ACU | 4 | 2 | 1 | 1 | 2 | 10 | 20 | 9 |
| Gln | CAA | 1 | 2 | 3 | 3 | 0 | 9 | 7 | 17 | | ACC | 10 | 9 | 8 | 3 | 4 | 35 | 26 | 23 |
| | CAG | 7 | 5 | 7 | 1 | 3 | 24 | 32 | 32 | | ACA | 3 | 1 | 1 | 0 | 0 | 5 | 3 | 6 |
| Glu | GAA | 10 | 5 | 5 | 5 | 3 | 29 | 63 | 40 | | ACG | 6 | 9 | 7 | 2 | 2 | 27 | 5 | 15 |
| | GAG | 7 | 3 | 2 | 0 | 3 | 15 | 20 | 19 | Trp | UGG | 5 | 2 | 1 | 1 | 1 | 10 | 5 | 13 |
| Gly | GGU | 1 | 1 | 2 | 1 | 0 | 5 | 43 | 24 | Tyr | UAU | 8 | 6 | 8 | 2 | 3 | 28 | 6 | 18 |
| | GGC | 15 | 16 | 13 | 7 | 7 | 59 | 33 | 27 | | UAC | 11 | 10 | 11 | 0 | 2 | 35 | 19 | 12 |
| | GGA | 3 | 4 | 3 | 0 | 2 | 12 | 1 | 8 | Val | GUU | 2 | 1 | 1 | 1 | 0 | 5 | 37 | 21 |
| | GGG | 0 | 1 | 3 | 0 | 0 | 4 | 3 | 13 | | GUC | 10 | 7 | 6 | 6 | 3 | 33 | 8 | 13 |
| His | CAU | 3 | 4 | 1 | 1 | 2 | 11 | 4 | 18 | | GUA | 3 | 1 | 2 | 1 | 0 | 7 | 23 | 9 |
| | CAC | 3 | 2 | 3 | 1 | 2 | 11 | 14 | 11 | | GUG | 4 | 5 | 2 | 4 | 2 | 17 | 16 | 24 |
| Ile | AUU | 3 | 3 | 3 | 0 | 0 | 9 | 13 | 30 | End | UAA | — | — | — | — | — | 0 | ND[d] | ND |
| | AUC | 7 | 8 | 9 | 2 | 4 | 31 | 15 | 23 | | UAG | 1 | — | — | — | — | 1 | ND | ND |
| | AUA | 0 | 1 | 4 | 0 | 2 | 7 | 0.4 | 5 | | UGA | — | 1 | 1 | 1 | 1 | 4 | ND | ND |
| Leu | UUA | 0 | 1 | 0 | 0 | 0 | 1 | 2 | 14 | fMet | AUG | 1 | 1 | 1 | — | 1 | 4 | ND | ND |
| | UUG | 1 | 2 | 3 | 2 | 3 | 11 | 3 | 12 | | GUG | — | — | — | 1 | — | 1 | ND | ND |
| | CUU | 1 | 2 | 2 | 1 | 1 | 7 | 5 | 14 | | | | | | | | | | |
| | CUC | 4 | 7 | 5 | 3 | 4 | 24 | 6 | 13 | | | | | | | | | | |
| | CUA | 0 | 1 | 0 | 0 | 0 | 1 | 1 | 4 | | | | | | | | | | |
| | CUG | 5 | 9 | 14 | 9 | 10 | 48 | 66 | 56 | | | | | | | | | | |

[a]Absolute codon usage for the subunit cistrons include the signal peptides (see Table 2). The number of codons in the five individual subunits are 269(S1), 227(S2), 228(S3), 132(S4), and 121(S5).
[b]Data deduced from Grosjean and Fiers Gene 18:199, 1982. S = strongly expressed genes; W = moderately to weakly expressed genes.
[c]Relative codon usage per 1000 codons. Pertussis usage based on 977 codons for the pertussis toxin gene (PTX). E. coli usage based on 5253 codons for highly expressed genes (S) and 5231 codons for moderate to weakly expressed genes (W).
[d]ND not determined.

The assignment for S1 in the location shown in FIG. 4d is further supported by a significant homology of two regions in the S1 amino acid sequence with two related regions in the A subunits of both cholera and E. coli heat labile toxins. These homologous regions, shown in Table 4, may be part of functional domains for a catalytic activity in the subunits for all three toxins. Furthermore, the assignment for S1, as well as the correct prediction of the signal peptide cleavage site, is supported by preliminary amino acid sequence data for the mature protein (unpublished results).

Subunits S2 and S3 share 70% amino acid homology, which makes the correct assignment of these subunits to their ORFs difficult if it is based only on the amino acid composition and the molecular weight. Nevertheless, the gene order could be determined as shown in FIG. 4d based on the location of a Tn5-induced mutation responsible for the lack of active pertussis toxin in the supernatant of the mutant B. pertussis strains. This Tn5 insertion was mapped 1.3 kb downstream of the start site for the S4 subunit gene, as indicated by the arrow in FIG. 4a. As can be seen in FIG. 4, the Tn5-insertion in those mutants would be located in the ORF for S3. Although unable to produce active pertussis toxin, the mutants are still able to produce the S2 subunit. Thus, the Tn5-insertion in those mutants is not located in the structural gene for S2. Therefore, the ORFs for S2 and S3 could be differentiated.

Amino acid sequences

The amino acid sequence for each subunit was deduced from the nucleotide sequence and is shown in Table 2. The mature proteins contain 234 amino acids for S1, 199 amino acids for S2, 110 amino acids for S4, 100 amino acids for S5 and 199 amino acids for S3, in the order of the gene arrangement from the 5'-end to the 3'-end. Most likely all subunits contain signal peptides, as expected for secretory proteins. The length of the putative signal peptides was estimated after analysis of the hydrophobicity plot, the predicted secondary structure and application of von Heijne's rule for the prediction of the most probable signal peptide cleavage site. The cleavage site for each subunit is shown in Table 2 by the asterisks. The correct prediction of the cleavage sites for S4 and S1 (unpublished) was confirmed by amino terminal sequencing of the purified mature subunits. The length of the signal peptides varies from 34 residues for S1, 28 residues for S3, and 27 residues for S2, to 21 residues for S4, and 20 residues for S5. All of the signal peptides contain a positively-charged amino terminal region of variable length, followed by a sequence of hydrophobic amino acids, usually in α-helical or partially α-helical, partially β-pleated conformation. A less hydrophobic carboxy-terminal region follows, usually ending in a β-turn conformation at the signal peptide cleavage site. All subunits except S5 follow the −1, −3 rule, which positions the cleavage site after Ala-X-Ala. The amino-terminal charge for the subunit signal peptides varies between +4 for S1 and +1 for S4 and S5. All described properties correspond very well to the general properties for bacterial signal peptides.

Two different initiation codons are used for the translation of all subunits in B. pertussis, i.e., the most frequently used ATG for S1, S2, S3 and S5, and the less frequently used GTG for S4. The codon usage (Table 4) is unsuitable for efficient translation of the pertussis toxin gene in E. coli.* This is reflected by the codon choice for frequently used amino acids, such as alanine, arginine, glycine, histidine, lysine, proline, serine and valine. Whether pertussis toxin is a strongly or weakly expressed protein in *B. pertussis* and whether this expression is regulated by the presence of a precise relative amount of the different tRNA isoacceptors, possibly different from *E. coli,* remains to be established. This can be evaluated by *in vitro* translation using *E. coli* and B. pertussis cell free . extracts.

Closer examination of the amino acid sequence reveals the striking absence of lysines in S1. Another interesting feature is the overall relatively high amount of cysteines as compared to *E. coli* proteins. Cysteines do not seem to be involved in inter-subunit links to construct the quaternary structure of the toxin, since all subunits can be easily separated by SDS-PAGE in the absence of reducing agents. Most likely, the cysteines are involved in intrachain bonds, since reducing agents significantly change the electrophoretic mobility of all subunits but S4. Serines, threonines and tyrosines also are represented more frequently than in average *E. coli* proteins. The hydroxyl groups of these residues may be involved in the quaternary structure through hydrogen bonding.

Analysis of the flanking regions

Since all pertussis toxin subunits are closely linked and probably expressed in a very precise ratio, it is possible that they are arranged in a polycistronic operon. A polycistronic arrangement for the subunit cistrons also has been described for other bacterial toxins bearing similar enzymatic functions, such as diphtheria, cholera and *E. coli* heat labile toxins. Therefore, the flanking regions were analyzed for the presence of transcriptional signals. In the 5′ flanking region, starting at position 469, the sequence TAAAATA was found, which matches six of the seven nucleotides found in the ideal TATAATA Pribnow or $-10$ box. An identical sequence can be found in several other bacterial promotors, including the lambda L57 promotor. Given the fact that most transcripts start at a purine residue about 5–7 nucleotides downstream from the Pribnow box, the transcriptional start site was tentatively located at the adenine residue at position 482. This residue is located in the sequence CAT, often found at transcriptional start sites. Upstream from the proposed $-10$ box, the sequence CTGACC starts at position 442. This sequence matches four of the six nucleotides found in the ideal *E. coli* $-35$ box TTGACA. The mismatching nucleotides in the proposed pertussis toxin $-35$ box are the two end nucleotides, of which the 3′ residue is the less important nucleotide in the *E. coli* $-$35 consensus box. A replacement of the T by a C in the first position of the consensus sequence can also be found in several *E. coli* promotors. The distance between the two proposed promotor boxes is 21 nucleotides, a distance of the same length has been found in the galPl promotor and in several plasmid promotors. The proposed $-35$ box is immediately preceded by two overlapping short inverted repeats with calculated free energies of $-15.6$ kcal and $-8.6$ kcal, respectively. Inverted repeats can also be found at the 5′-end of the cholera toxin promotor. In both cases, they may be involved in positive regulation of the toxin promotors. None of the ORFs assigned to the other subunit is closely preceded by a similar promotor-like structure. However, a different promotor-like structure was found associated with the S4 subunit ORF.

The 3′-flanking region has been examined for the presence of possible transcriptional termination sites. Several inverted repeats could be found; the most significant is located in the region extending from position 4031 to 4089 and has a calculated free energy of $-41.4$ kcal. None of the inverted repeats are immediately followed by an oligo(dT) stretch, which may suggest that they function in a rho-dependent fashion. Preliminary experiments indicate, however, that neither inverted repeat functions efficiently in *E. coli* (results not shown). Whether they are functional in *B. pertussis* remains to be established and can be investigated by a small deletion or site-directed mutagenesis experiments, which are feasible now that the DNA sequence is known. Another possibility is that the five different subunits may not be the only proteins encoded in the polycistronic operon and that cistrons for other peptides, possibly involved in regulation, assembly or transport, are cotranscribed. Non-structural proteins involved in the posttranslational processing of *E. coli* heat labile toxin have been proposed. However, no significantly long ORF was found at the 3′-end of the nucleotide sequence shown in FIG. 4*b*. If other proteins are encoded by the same polycistronic operon, their coding regions must be located further downstream.

Additionally, the 5′-flanking region of each cistron was also examined for the presence of ribosomal binding sites. Neither the ribosomal binding sequences for *B. pertussis* genes, nor the 3′-end sequence of the 16 S rRNA are known. Therefore, the flanking regions could be compared with only the ribosomal binding sequences of heterologous procaryotic organisms represented by the Shine-Dalgarno sequence. Preceding the S1 initiation codon, the sequence GGGGAAG was found starting at position 495. This sequence shares four out of seven nucleotides with the ideal Shine-Dalgarno sequence AAGGAGG. The two first mismatching nucleotides in the pertussis toxin gene would not destabilize the hybridizatin to the 3′-end of the *E. coli* 16 S rRNA. This putative ribosomal binding site is close enough to the initiation codon for S1 to be functional in E. coli. Another possible Shine-Dalgarno sequence overlaps the first one and also matches four out of seven nucleotides to the consensus sequence. The mismatching nucleotides, however, have a more destabilizing effect than the ones found in the first sequence. The S2 subunit ORF is not closely preceded by a ribosomal binding sequence, which may suggest that S2 is translated through a mechanism not involving the detachment and reattachment of the ribosome between the coding regions for S1 and S2. The short distance between the S1 and S2 cistrons, and the absence of a ribosomal binding site are characteristic of this mechanism. A ribosomal binding site for S4 in the sequence CAGGGCGGC, starting at position 2066 is possible. The ORF for S5 is preceded by the sequence AAGGCG, starting at position 2485, which matches five out of six nucleotides in the consensus sequence AAGGAG. Finally, S3 is preceded by the sequence GGGAACAC, which is very similar to the proposed ribosomal binding site for S1, i.e., GGGAAGAC.

Taken as a whole, the results described herein clearly establish the complete nucleotide sequence of all structural cistrons for pertussis toxin. The gene order, as shown in FIG. 4, is S1, S2, S4, S5, and S3. The calculated molecular weights from the deduced sequence of the mature peptides are 26,024 for S1; 21,924 for S2; 12,058 for S4; 11,013 for S5 and 21,873 for S3. Since S4 is present in two copies per toxin molecule, the total molecular weight for the holotoxin is about 104,950. This is in agreement with the apparent molecular weight estimated by non-denaturing PAGE. The most striking feature of the predicted peptide sequences is the high homology between S2 and S3. The two peptides share 70% amino acid homology and 75% nucleotide homology. This suggests that both cistrons were generated through a duplication of an ancestral cistron followed by mutations which result in functionally-different peptides. The differences between S2 and S3 are scattered throughout the whole sequence and are slightly more frequent in the amino-terminal half of the peptides. Despite their high homology, also reflected in the predicted secondary structures and hydrophilicities, S2 and S3 subunits cannot substitute for each other in the functionally-active pertussis toxin. The comparison between the two subunits may be useful in localizing their functional domains in relation to their primary, secondary and tertiary structure. On the basis of the differences, S2 and S3 are divided into two domains, the amino-terminal and the carboxy-terminal. Each of the subunits binds to a S4 subunit. This function could be located in the more conserved carboxy-terminal domains of S2 and S3. The two resulting dimers are thought to bind to one S5 subunit. This function could be assigned to the more divergent amino-terminal domains of S2 and S3. Alternatively, it is possible that the dimers bind to the S5 subunit through S4 and that the amino-terminal domains of S2 and S3 are involved in some other function, possibly the interaction of the binding moiety (S2 through S5) with the enzymatically-active moiety (S1).

The enzymatically-active S1 subunit was compared to the A subunits of other bacterial toxins. Two regions with significant homology to cholera and E. coli heat labile toxins were found (Table 4). They are tandemly located in analogous regions of all three toxins. However, the three amino acid differences found in these regions cannot be explained by single base pair changes in the DNA. Furthermore, in most cases the homologous amino acids use quite different codons in pertussis toxin compared to cholera and E. coli heat labile toxins. This, together with the fact that no other significant homology in the primary structure could be found and that the amino acid sequences of the other subunits are completely different from the sequence of any other ADP-ribosylating toxin, strongly suggests that pertussis toxin is not evolutionarily related to any of the other known bacterial toxins. The limited homology of S1 subunit to the A subunits of cholera and E. coli heat labile toxins could be due to convergent evolution, since all three toxins contain a very similar enzymatic activity and use a relatively closely-related acceptor substrate (Ni protein for pertussis toxin and Ns protein for cholera and E. coli heat labile toxins). The NAD-binding site for the two enterotoxins has been identified at the carboxy-terminal region of their A1 subunit. No significant homology could be found between the carboxy-terminal of the enterotoxins, nor any other NAD-binding enzymes, and the analogous region in the S1 subunit. This suggests that the NAD-binding function of the ADP-ribosylating enzymes is dependent more on the secondary or tertiary structures, than on the primary structures. It is proposed that the two enzymatically-active domains lie in different regions of the protein, one at the amino-terminal half of the subunit for the acceptor substrate (Ni) binding and the other at the carboxy-terminal half of the subunit for the donor substrate (NAD+) binding.

The presence of a promotor-like structure upstream of the S1 subunit cistron and possible transcriptional termination signals downstream of the S3 subunit cistron suggests that pertussis toxin, like many other bacterial toxins, is expressed through a polycistronic mRNA. The inverted repeats immediately preceding the proposed promotor may be sites for positive regulation of expression of the toxin in B. pertussis. Evidence for a positive regulation came through the discovery of the vir gene, the product of which is essential for the production of many virulence factors, including pertussis toxin. Recent evidence in our laboratory suggests that the proposed inverted repeats in the 3' flanking region are not very efficient in transcriptional termination in E. coli (results not shown). The termination of transcription in B. pertussis may be carried out by a slightly different mechanism than in E. coli; on the other hand, the polycistron may contain other, not yet identified, genes related to expression of functionally-active pertussis toxin or other virulence factors. We have described a promotor-like structure preceding subunit S4 and possible termination signals following the S4 cistron. The S4 promotor-like structure is quite different from the proposed promotor at the beginning of S1 subunit. It is part of an inverted repeat, suggesting an iron regulation of the S4 subunit expression. This is supported by the fact that chelating agents stimulate the accumulation of active pertussis toxin in cell supernatants. It is thus possible that pertussis toxin is expressed efficiently by two dissimilar promotors, one (promotor 1) located in the 5'-flanking region and the other (promotor 2) located upstream of S4. Both promotors would be regulated by different mechanisms. Promotor 1 would be positively regulated, possibly by the vir gene product, and promotor 2 would be negatively regulated by the presence of iron. In optimal expression conditions, such as in the presence of the vir gene product and in the absence of iron, the S4 subunit cistron would be transcribed twice for every transcription of the other subunits. This is a mechanism that would explain the stoichiometry of the pertussis toxin subunits of 1:1:1:2:1 for S1:S2:S3:S4:S5, respectively, in the biologically active holotoxin.

Attempts to express the pertussis toxin gene in E. coli have been heretofore unsuccessful, although very sensitive monoclonal and polyclonal antibodies are available. This lack of expression in E. coli may reside in the fact that B. pertussis promotors are not efficiently recognized by the E. coli RNA polymerase. Analysis of the promotor-like structures of the pertussis toxin gene and their comparison to strong E. coli promotors show very significant differences, indeed, of which the most striking ones are the unusual distances between the proposed −35 and −10 boxes in the pertussis toxin promotors.

The distance between those two boxes in strong *E. coli* promotors is around 17 nucleotides, whereas the distances in the two putative pertussis toxin promotors are 21 nucleotides for the polycistronic promotor and 10 nucleotides for the S4 subunit promotor. Preliminary results in our laboratory using expression vectors designed to detect heterologous expression signals which are able to function in *E. coli* further indicate that *B. pertussis* promotors may not be recognized by the *E. coli* expression machinery. In addition, the codon usage for pertussis toxin is extremely inefficient for translation in *E. coli* (Table 5). Preliminary experiments show that the insertion of a fused lac/trp promotor in the KpnI site upstream of the pertussis toxin operon probably enhances transcription but does not produce detectable levels of pertussis toxin (unpublished results). Efficient expression in *E. coli* would require resynthesis of the pertussis toxin operon, respecting the optimal codon usage for *E. coli*. It is not known whether the codon usage for pertussis toxin reflects the optimal codon usage for expression in *B. pertussis*, since no other *B. pertussis* gene has heretofore been sequenced.

The cloned and sequenced pertussis toxin genes are useful for the development of an efficient and safer vaccine against whooping cough. By comparison to other toxin genes with similar biochemical functions and by physical identification of the active sites either for the ADP-ribosylation in the S1 subunit or the target cell binding in subunits S2 through S4, it is now possible to modify those sites by site-directed mutagenesis of the *B. pertussis* genome. These modifications could abolish the pathobiological activities of pertussis toxin without hampering its immunogenicity and protectivity. Alternatively, knowing the DNA sequence, mapping of eventual protective epitopes is now made possible. Synthetic oligopeptides comprising those epitopes will also be useful in the development of a new generation vaccine.

It is understood that the examples and embodiments described herein are for illustrative purposes only and that various modifications or changes in light thereof will be suggested to persons skilled in the art and are to be included within the spirit and purview of this application and the scope of the appended claims. The theories suggested herein are only reasonable explanations based on the current knowledge and facts and are propounded without in any manner being bound to them.

We claim:

1. An isolated gene consisting essentially of DNA encoding pertussis toxin.
2. A recombinant DNA vector containing the gene of claim 1.
3. An *E. coli* containing the recombinant DNA vector of claim 2.

* * * * *